(12) United States Patent
Rahman et al.

(10) Patent No.: US 8,771,149 B2
(45) Date of Patent: Jul. 8, 2014

(54) COMPLIANCE MONITOR AND METHOD FOR A MEDICAL DEVICE

(75) Inventors: Tariq Rahman, Moylan, PA (US); Thomas H. Shaffer, Chadds Ford, PA (US); J. Richard Bowen, Wilmington, DE (US)

(73) Assignee: The Nemours Foundation, Jacksonville, FL (US)

( * ) Notice: Subject to any disclaimer, the term of this patent is extended or adjusted under 35 U.S.C. 154(b) by 2634 days.

(21) Appl. No.: 11/369,994

(22) Filed: Mar. 8, 2006

(65) Prior Publication Data

US 2006/0166157 A1    Jul. 27, 2006

Related U.S. Application Data

(63) Continuation-in-part of application No. 11/025,783, filed on Dec. 30, 2004, now Pat. No. 7,166,063, which is a continuation of application No. 10/260,526, filed on Oct. 1, 2002, now Pat. No. 6,890,285.

(60) Provisional application No. 60/325,565, filed on Oct. 1, 2001, provisional application No. 60/384,112, filed on May 31, 2002.

(51) Int. Cl.
*A63B 24/00* (2006.01)

(52) U.S. Cl.
USPC ................................ 482/8; 482/11; 433/27

(58) Field of Classification Search
USPC ............ 482/1–11, 900–902; 433/5, 6, 25, 27
See application file for complete search history.

(56) References Cited

U.S. PATENT DOCUMENTS

| | | | | |
|---|---|---|---|---|
| 3,885,310 | A * | 5/1975 | Northcutt | 433/5 |
| 4,255,138 | A * | 3/1981 | Frohn | 433/6 |
| 4,764,111 | A | 8/1988 | Knierim | |
| 4,952,928 | A | 8/1990 | Carroll et al. | |
| 5,204,670 | A | 4/1993 | Stinton | |
| 5,245,592 | A | 9/1993 | Kuemmel et al. | |
| 5,543,780 | A | 8/1996 | McAuley et al. | |
| 5,626,537 | A | 5/1997 | Danyo et al. | |
| 5,651,671 | A * | 7/1997 | Seay et al. | 433/5 |
| 5,774,425 | A | 6/1998 | Ivanov et al. | |
| 5,980,246 | A | 11/1999 | Ramsay et al. | |
| 6,099,303 | A * | 8/2000 | Gibbs et al. | 433/5 |
| 6,154,676 | A | 11/2000 | Levine | |
| 6,212,435 | B1 | 4/2001 | Lattner et al. | |
| 6,334,073 | B1 | 12/2001 | Levine | |
| 6,436,058 | B1 | 8/2002 | Krahner et al. | |
| 6,515,593 | B1 | 2/2003 | Stark et al. | |
| 6,540,707 | B1 | 4/2003 | Stark et al. | |
| 6,611,783 | B2 | 8/2003 | Kelly et al. | |
| 6,616,579 | B1 | 9/2003 | Reinbold et al. | |
| 6,623,698 | B2 | 9/2003 | Kuo | |
| 6,624,752 | B2 | 9/2003 | Klitsgaard et al. | |
| 6,702,765 | B2 | 3/2004 | Robbins et al. | |
| 7,036,514 | B2 | 5/2006 | Heck | |
| 7,553,157 | B2 * | 6/2009 | Abolfathi et al. | 433/6 |
| 2006/0068353 | A1 | 3/2006 | Abolfathi et al. | |

* cited by examiner

*Primary Examiner* — Glenn Richman
(74) *Attorney, Agent, or Firm* — Drinker Biddle & Reath LLP

(57) ABSTRACT

An orthodontic compliance monitor includes a sensor that senses when an orthodontic appliance is properly positioned and a processor that processes an output of the sensor and generates compliance data. A memory device stores compliance data and the processor generates the compliance data based on a compliance protocol. System and methods for orthodontic compliance are also disclosed.

43 Claims, 13 Drawing Sheets

COMPLIANCE MONITOR AND METHOD FOR A MEDICAL DEVICE

CROSS-REFERENCE TO RELATED APPLICATIONS

This application is a continuation in part of U.S. patent application Ser. No. 11/025,783, filed on Dec. 30, 2004 now U.S. Pat. No. 7,166,063, which is a continuation of U.S. patent application Ser. No. 10/260,526 filed Oct. 1, 2002, now U.S. Pat. No. 6,890,285, which issued on May 10, 2005, which claims priority under 35 U.S.C. §119(e) to U.S. Provisional Application No. 60/325,565, filed Oct. 1, 2001 and U.S. Provisional Application No. 60/384,112, filed May 31, 2002, all of which are incorporated herein by reference in their entireties.

BACKGROUND OF THE INVENTION

1. Field of the Invention

The invention is directed generally to medical compliance monitor devices and medical compliance monitoring methods and, more particularly, directed to an orthodontic compliance monitor and method that provides compliance feedback.

2. Related Art

Medical compliance is a significant issue in the care and treatment of many disorders. Failure of a patient to comply with a health care provider's instructions to wear a medical device in a prescribed way or for a prescribed period of time inhibits the care of the patient. In addition to slow recovery or treatment, non-compliance by the patient leads to increased health-care costs. In some instances, non-compliance can lead to additional complications requiring additional care and treatment.

There have been previous attempts to use compliance monitors outfitted in medical devices with a sensor for detecting when the patient is wearing the medical device. However, none of these attempts have been for orthodontic devices. These non-orthodontic device monitors operate in substantially dry conditions and are not greatly limited by size, or the other conditions typically present in a patient's mouth such as bacteria, saliva, pH, etc.

The determination of compliance in orthodontic devices is important to ensure oral health. Many orthodontic devices, such as braces, need to changed, modified, or replaced roughly based on a period of time a patient uses the orthodontic device. In this regard, the non-compliant usage of the device may be detrimental when the orthodontic device is changed, modified, or replaced during the course of treatment. Heretofore, the use of compliance monitors in orthodontic devices has not been feasible because the use of such devices could not take place in the mouth environment could not be sized to effectively operate, and/or could not effectively determine compliance.

Moreover, many devices are unable to provide feedback to the patient regarding compliance. It would be further advantageous to have a compliance monitor that provides the patient with instant, immediate, or readily available feedback on whether the patient is in compliance with the prescribed treatment. In this way, non-compliance is recognized by the patient much earlier in treatment, providing the patient with the opportunity to correct compliance deficiencies.

Accordingly, there is a need for a method and apparatus that can determine compliance in the use of orthodontic devices, and that can provide feedback on compliance more readily than heretofore feasible.

SUMMARY OF THE INVENTION

The invention meets the foregoing needs and provides a method and apparatus that monitors compliance in the use of medical devices, such as orthodontic devices, and that furthermore includes other advantages apparent from the discussion herein.

The invention may be implemented in a number of ways. According to one aspect of the invention an orthodontic compliance monitor, includes a sensor that senses when an orthodontic appliance is positioned in the mouth for use, a processor that processes an output of the sensor and generates compliance data based on a compliance protocol, and a memory device that stores the compliance data.

The sensor may include at least one of a temperature sensor, pressure sensor, moisture sensor, light sensor, or pH sensor. The processor may include at least one of a micro controller, microprocessor, application specific integrated circuit, counter, or field programmable gate array. The orthodontic compliance monitor further may include an interface configured to output the compliance data as at least one of radio frequency signals, optical signals, or electrical signals. The orthodontic compliance monitor further may include an output device configured to output compliance data. The output device may include a display that displays the compliance data. The compliance protocol may include an amount of time the orthodontic appliance is to be worn over a period of time. An orthodontic appliance may be combined with the orthodontic compliance monitor. The orthodontic appliance may be one of an orthodontic brace, a retainer, a mouth guard, a bruxism treatment device, and a nightguard. The compliance monitor may be configured to be at least one of removably coupled with an orthodontic appliance or physically incorporated into an orthodontic appliance.

According to another aspect of the invention a method of determining whether a user is using an orthodontic appliance includes the steps of sensing when an orthodontic appliance is positioned for use in a user's mouth to generate an output, processing the output and generating compliance data based on a compliance protocol, and storing the compliance data.

The step of sensing may include sensing at least one of temperature, pressure, moisture, light, or pH. The method may further include the step of transmitting the compliance data as at least one of radio frequency signals, optical signals, or electrical signals. The method may further include the step of displaying the compliance data.

In yet another aspect of the invention a computerized orthodontic compliance system, includes a sensor that senses when an orthodontic appliance is positioned in the mouth for use, a processor that processes an output of the sensor and generates compliance data based on a compliance protocol, a memory that stores the compliance data, and a computer configured to receive the compliance data from the memory.

The system may further include an interface configured to output the compliance data as at least one of radio frequency signals, optical signals, or electrical signals to the computer. The sensor may include at least one of a temperature sensor, pressure sensor, moisture sensor, light sensor, or pH sensor. The processor may include at least one of a micro controller, microprocessor, application specific integrated circuit, counter, or field programmable gate array. The system may further include an interface configured to transmit the compliance data as at least one of radio frequency signals, optical signals, or electrical signals. The system may further include an output device configured to output the compliance data.

In another aspect of the invention a computer readable medium having computer executable code that executes orthodontic compliance monitor processing includes sensing when an orthodontic appliance is positioned in the mouth for use to generate an output, processing the output and generating compliance data based on a compliance protocol, and storing compliance data.

The compliance monitor processing may further include transmitting the compliance data as at least one of radio frequency signals, optical signals, or electrical signals. The compliance monitor processing may further include displaying the compliance data.

In yet another aspect of the invention an orthodontic compliance monitor includes means for sensing when an orthodontic appliance is positioned in the mouth for use, means for processing an output of the sensor means and for generating compliance data based on a compliance protocol, and means for storing the compliance data.

In another aspect of the invention an orthodontic appliance compliance monitor, includes an orthodontic appliance including one of an orthodontic brace, a retainer, a mouth guard, a bruxism treatment device, and a nightguard, and means for determining when an orthodontic appliance is positioned in the mouth for use arranged on the orthodontic appliance, the determining means includes one of a sensor or reactive chemical.

Additional features, advantages, and embodiments of the invention may be set forth or apparent from consideration of the following detailed description, drawings, and claims. Moreover, it is to be understood that both the foregoing summary of the invention and the following detailed description are exemplary and intended to provide further explanation without limiting the scope of the invention as claimed.

BRIEF DESCRIPTION OF THE DRAWINGS

The accompanying drawings, which are included to provide a further understanding of the invention, are incorporated in and constitute a part of this specification, illustrate embodiments of the invention and together with the detailed description serve to explain the principles of the invention. No attempt is made to show structural details of the invention in more detail than may be necessary for a fundamental understanding of the invention and the various ways in which it may be practiced. In the drawings.

DETAILED DESCRIPTION OF THE INVENTION

Figure 1:
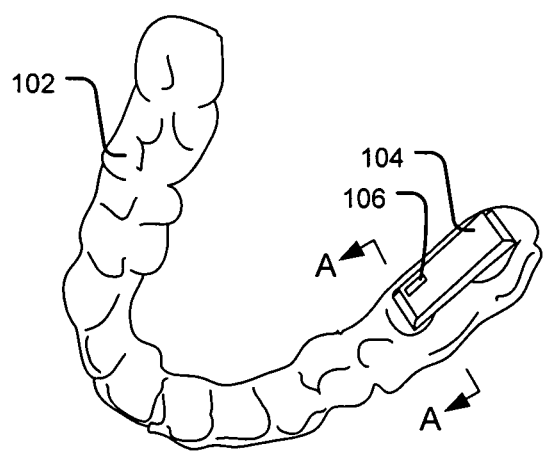
FIG. 1 schematically shows a first embodiment of an orthodontic device and compliance monitor constructed according to the principles of the invention with a sensor mounted on the outer surface of the device.

The embodiments of the invention and the various features and advantageous details thereof are explained more fully with reference to the non-limiting embodiments and examples that are described and/or illustrated in the accompanying drawings and detailed in the following description. It should be noted that the features illustrated in the drawings are not necessarily drawn to scale, and features of one embodiment may be employed with other embodiments as the skilled artisan would recognize, even if not explicitly stated herein. Descriptions of well-known components and processing techniques may be omitted so as to not unnecessarily obscure the embodiments of the invention. The examples used herein are intended merely to facilitate an understanding of ways in which the invention may be practiced and to further enable those of skill in the art to practice the embodiments of the invention. Accordingly, the examples and embodiments herein should not be construed as limiting the scope of the invention, which is defined solely by the appended claims and applicable law. Moreover, it is noted that like reference numerals represent similar parts throughout the several views of the drawings.

With reference now to FIGS. 1-8 and 11, there is shown schematically various embodiments of a medical device compliance monitor 104 of the invention arranged with a medical device 102, such as an orthodontic brace, which may be positioned on one or more teeth 1 and/or surrounding gum tissue 2 (not shown in FIG. 1) as is known in the art. For example, one type of orthodontic brace with which the invention may be employed is marketed by Align Technology, Inc. Santa Clara, Calif., under the INVISALIGN trade name.

The medical device compliance monitor 104 includes a compliance sensor 106. The compliance sensor 106 is a sensor that can distinguish when the medical device is being properly used by and/or is on or off of the patient. Accordingly, the compliance monitor 104 provides the patient and/or doctor information with respect to the medical device usage to ensure proper and prudent medical care based on what is sensed by the compliance sensor 106.

The orthodontic braces shown in FIGS. 1-8 and 11 may be of the type that are constructed of a synthetic medical grade plastic material. Such orthodontic braces are routinely adjusted or replaced in order to apply pressure to the teeth to address malocclusion or other conditions known in the art. Although the Figures and descriptions focus on braces as an example, the invention is equally applicable to other orthodontic devices including retainer devices, bruxism devices, nightguards, athletic mouthguards or the like.

Figure 2:
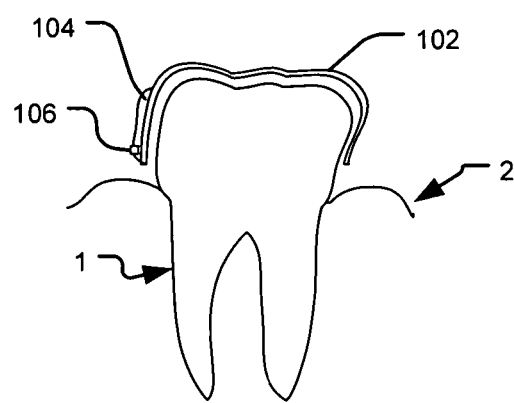
FIG. 2 shows a cross-section of the orthodontic device and compliance monitor of FIG. 1 taken along lines A-A.

Suitable compliance sensors include, but are not limited to temperature sensors, pressure sensors, moisture sensors, light sensors, pH sensors, and the like. With respect to a temperature sensor, the temperature sensor may distinguish when the medical device 102 is being worn by monitoring the temperature at a point near or on the medical device as shown in FIG. 2 by the compliance sensor 106 position. When the medical device 102 is being used, the temperature may be elevated relative to ambient temperature conditions. If the medical device is not being worn and/or is not in proper position, the temperature detected through the temperature sensor may be closer to ambient temperature than body temperature. Thus, for example, sensing a temperature at or near body temperature is indicative of properly wearing the medical device 102 and thus compliance.

The temperature may be sensed through the use of a thermistor or thermocouple type of sensor. For example, Negative Temperature Coefficient (NTC) thermistors may be used. These sensors exhibit decreasing electrical resistance with increases in environmental temperature and increasing electrical resistance with decreasing temperature. Positive Temperature Coefficient (PTC) thermistors may also be used and these sensors exhibit increasing electrical resistance with increases in environmental temperature and decreasing electrical resistance with decreasing temperature. Accordingly, the compliance monitor may sense the resistance across the compliance sensor 106 implemented as a thermistor to determine a temperature and thus compliance. When the resistance across the thermistor compliance sensor 106 is below or above a predetermined resistance, indicative of body temperature, then the compliance monitor 104 will register that the medical device is currently in place and/or proper position.

Thermocouple-type sensors may also be used. Thermocouples operate based on the Seebeck effect, which occurs in electrical conductors that experience a temperature gradient along their length. It should be apparent that any type of temperature probe including noncontact infrared (IR) thermometers may be used to determine the temperature for the compliance monitor 104 of the invention.

Figure 3:
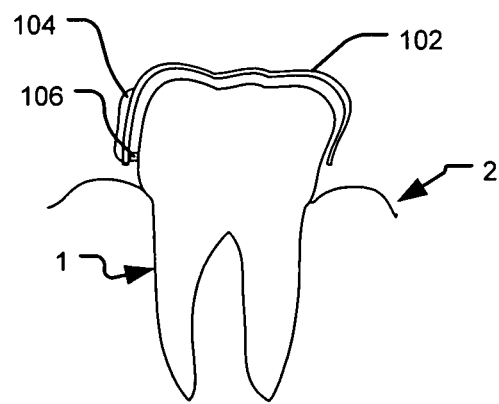
FIG. 3 shows a cross-section of a second embodiment of the orthodontic device and compliance monitor of the invention having a sensor mounted on an inner surface of the device.
Figure 4:
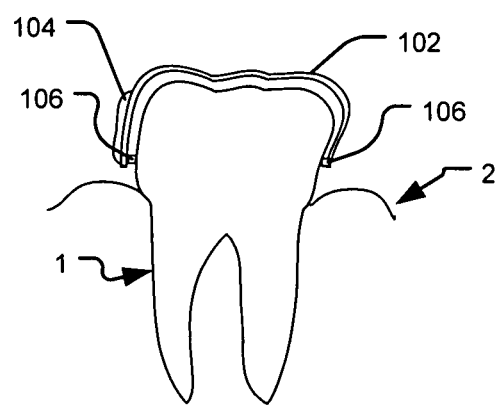
FIG. 4 shows a cross-section of a third embodiment of the orthodontic device and compliance monitor of the invention having multiple sensors mounted on an inner surface of the device.
Figure 5:
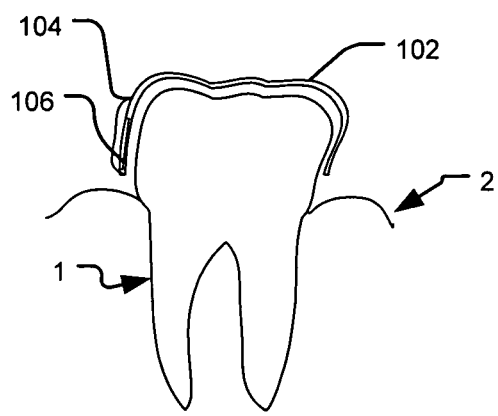
FIG. 5 shows a cross-section of a fourth embodiment of the orthodontic device and compliance monitor of the invention having an internal sensor structure.

Similarly, a pressure sensor may be arranged on the medical device 102 as shown in FIGS. 3-5 to determine when a person is properly wearing the medical device 102. In particular, the pressure sensor 106 may be arranged between a tooth and the device 102 as shown in FIGS. 3 and 4 to sense an increase in pressure between the medical device 102 and the teeth of the patient during chewing, installation, removal, wear or the like. For example, a pressure sensor may be arranged to sense the flexing of the medical device 102 as it is positioned onto the teeth. Alternatively, the pressure sensor 106 may be embedded in the medical device 102 as shown in FIG. 5. In this embodiment, the sensor may sense flexing of the medical device 102 as it is positioned onto the teeth or may sense an increase in pressure associated with a chewing action. The pressure sensor may be implemented as a strain gauge, load cell, piezoelectric sensor, accelerometer, microwave radar (such as a single-chip, direct conversion 1.6 GHz Doppler radars using 0.25 pm CMOS and BiCMOS), or the like.

Moisture sensors may be used as the sensor 106 to sense when the medical device 102 is in the mouth. Such sensors may include CMOS Humidity Sensors, Impedance Moisture Sensor Technology, electronic impedance or capacitive sensors that respond to varying levels of partial water vapor pressure, or the like.

Similarly, light sensors may be used to determine when the medical device 102 is in the mouth with optio-electronic sensors or charge coupled devices (CCD) that measure ambient light or sense an intermittent light source blocked when the orthodontic device is being worn. For example, as shown in FIG. 4, two sensors 106, 106 may be arranged as an emitter-receiver pair on the medical device 102. The emitter may be a LED light, and the receiver may be a light sensitive sensor such as a photo-diode. The light from the emitter may then be blocked when the medical device 102 is placed on the teeth.

In the same respect, the sensor 106 may be implemented as a pH sensor using the FIG. 2 arrangement that may sense the pH of the surroundings. This pH is then compared to a range of norms for saliva when the device 102 is used in the mouth. Such a sensor may be a pH sensor with an Ag—AgCl combination electrode. If the device 102 is used in another body location; the sensor is adapted for the pH of that environment. Alternatively, the sensor 106 may be implemented as a capacitive sensor that measures capacitance with respect to the medical device 102 and determines changes therein when in proximity to the body. The associated circuitry for each of these above-noted sensors is not shown or described for brevity. However, such circuitry is known in the art.

As noted above, the compliance sensor 106 may be arranged anywhere on the medical device 102 and may be connected to the compliance monitor 104 that collects and stores data from the compliance sensor 106. For example, FIGS. 1 and 2 show the sensor 106 on the outside of the device 102; FIG. 3 shows the sensor 106 on an inside surface of the device 102; FIG. 4 shows two opposing sensors 106 mounted on the inside surface of the device 102; and FIG. 5 shows a sensor 106 integrated in a wall portion of the medical device 102 that may sense, for example, flexing as noted above. Other sensor arrangements are contemplated for use in the invention and are within scope and spirit thereof.

In this regard, the sensor 106 may be arranged anywhere in or on the medical device 102. The size of the compliance monitor 104 may vary widely but is preferably as small as possible. The compliance monitor 104 may be of a size and configured such that it does not interfere with the operation or function of the medical device 102. For example, when used with an orthodontic brace, the monitor does not interfere with any oral activities such as talking or eating. Moreover, the compliance monitor 104 may be integrated into the medical device 102 or may be separately provided and attached thereto.

Additionally, the compliance monitor 104 may be arranged anywhere on or in communication with the medical device 102. For example, the compliance monitor 104 may be arranged on the medical device 102 as shown in FIG. 1 or may be embedded or integrated in the medical device 102 as shown in FIG. 8 such that the compliance monitor 104 is inside the medical device 102.

Figure 6:
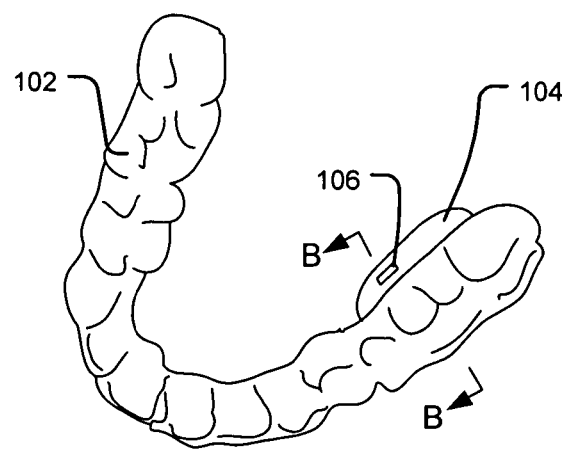
FIG. 6 shows yet another embodiment an orthodontic device and compliance monitor of the invention in which the compliance monitor is arranged adjacent to the orthodontic device.
Figure 7:
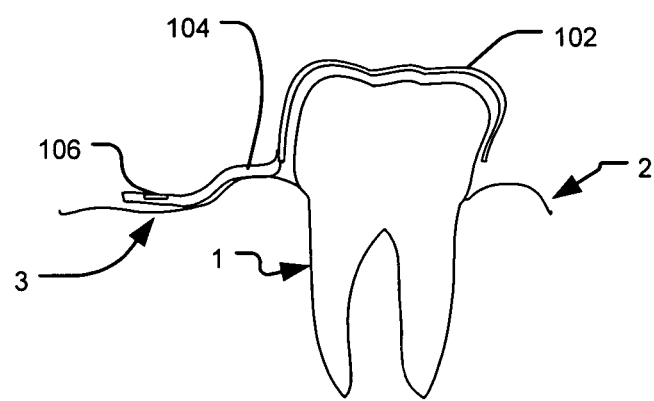
FIG. 7 shows a cross-section of the orthodontic device and compliance monitor of FIG. 6 taken along lines B-B.

Alternatively, the compliance monitor 104 may be connected to and extend from the medical device 102. With such an arrangement, the compliance monitor may be arranged in either a flexible or rigid packaging. This packaging may be contoured to mimic the roof of the mouth such that is may be comfortably arranged along the roof of the mouth 3 as shown in FIGS. 6 and 7. Also the compliance monitor could be packaged and contoured such that it may be arranged along the lower part of mouth.

The compliance monitor 104 may also be arranged anywhere in or on the patient that does not unduly interfere with bodily functions and be wirelessly in communication with the sensor 106 using any known RF communication protocol such as Bluetooth™.

Figure 8:
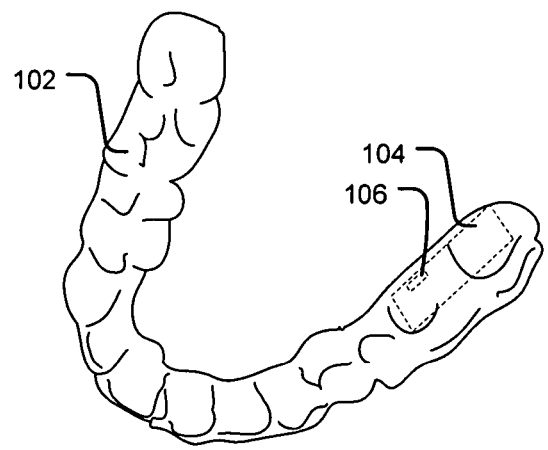
FIG. 8 shows another embodiment of an orthodontic device and compliance monitor of the invention in which the compliance monitor is arranged inside the orthodontic device.

FIG. 8 shows another embodiment of an orthodontic device and compliance monitor of the invention in which the compliance monitor is arranged inside the orthodontic device as noted above. In particular, the compliance monitor 104 may be embedded or integrated in the medical device 102.

Figure 9:
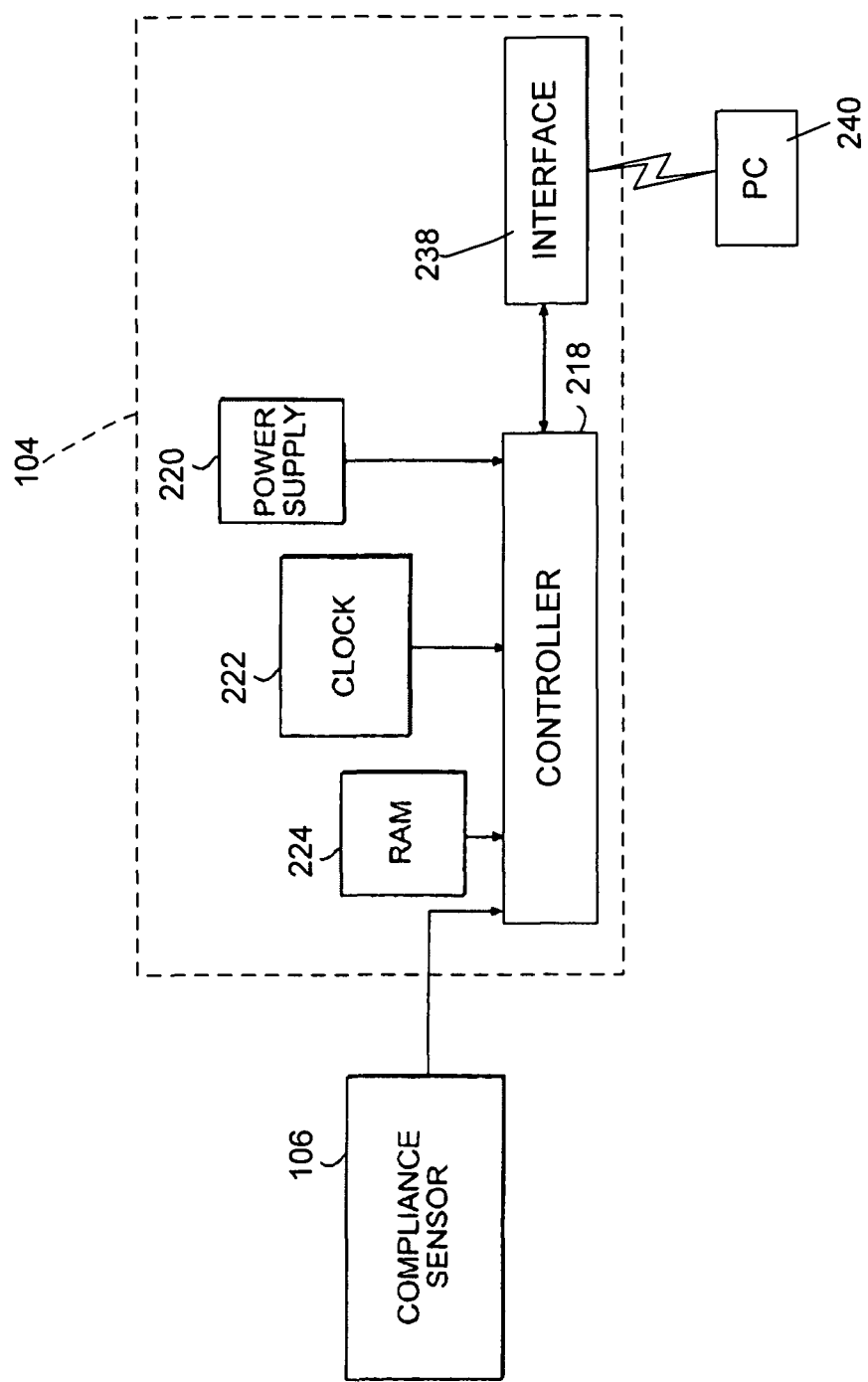
FIG. 9 shows an exemplary circuit for use with the invention to determine compliance.

With reference now to FIG. 9, the compliance monitor 104 may include a controller 218 connected to a power supply 220 such as one or more low-drain silver oxide batteries, a clock 222 and a non-volatile random access memory (RAM) 224. Input from the compliance sensor 106 may be received by the controller 218. The controller 218 may be connected through a computer interface 238, such as a serial connection or port for data transfer, as described below, with a computer, such as a Personal Computer (PC) 240 to provide compliance data to a medical care provider.

The controller 218 may receive data from the compliance sensor 106 as a function of time and compare the data with a compliance protocol using a software operating system to produce compliance data to determine if the collected data meets the requirements of the compliance protocol and thus, if the patient is in compliance with the protocol. The software operating system may be any known sensing function that interrogates a sensor to obtain a sensor output at a predetermined frequency and compares the sensor output to ascertain compliance for that time period and stores a result of the comparison.

The controller 218 may be implemented as a micro controller, microprocessor, application specific integrated circuit (ASIC), counter, field programmable gate array (FPGA) or the like. The controller may be programmed in the factory with the appropriate software operating system. Alternatively, as noted in the FIG. 10 embodiment, the software may be loaded after manufacture as discussed below. The controller 218 may take any known form to collect compliance data from the compliance sensor 106 and deliver the data to the PC 240 that may be located in the medical care provider's office. It should be noted that the PC 240 may be implemented as any known computer or processor such as a desktop PC, laptop PC, Apple™ based computer, or the like.

Figure 10:
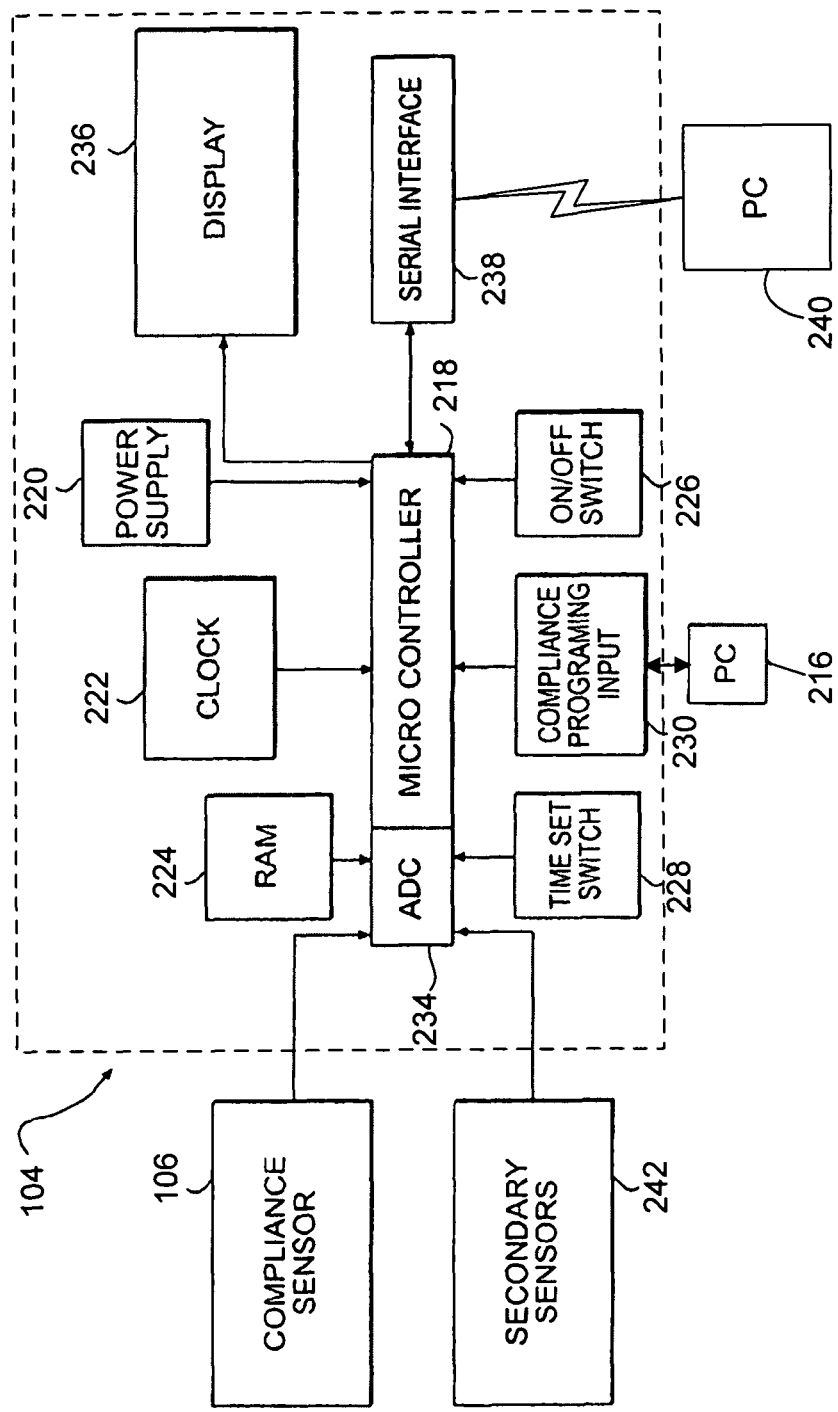
FIG. 10 shows another exemplary circuit for use with the invention to determine compliance that includes a display.

The interface 238 in the FIGS. 9 and 10 embodiments may operate using wired, wireless, or optical technology. More specifically, the compliance data may be sent to the PC 240 via wired connection via hard terminals. Alternatively, the compliance data may be transmitted wirelessly via any know radio frequency (RF) protocol/air interface including but not limited to Bluetooth™, wireless fidelity (Wi-Fi), radio frequency identification (RFID), or the like. The data may also be transmitted optically through any known technology such as infrared (IR) using for example any Infrared Data Association (IRDA) standard or the like. For example, the interface 238 may be responsive a hand-held infrared receiver module that may have a Universal Serial Bus (USB) connection to the PC 240. Although reference is made to a wireless protocol, any known protocol is within the scope of the invention. Moreover, any future enhancement of a current protocol or any future protocol is contemplated for use with the invention.

The controller 218 provides compliance output information such as data from the compliance sensor and compliance data to the PC 240 to display on the PC or other monitor (such as those shown in FIGS. 11-13 described below) whether compliance conditions are being met or not being met.

The controller 218 may be configured to not collect compliance data until the device is to be used. Accordingly, the controller 218 may be shipped in a "sleep mode" until needed. The controller 218 in such a case may be configured to transition out of a sleep mode when it senses compliance for the first time, when a portion of the medical device 102 is actuated, the battery connected, or the like.

With reference now to FIG. 10, the compliance monitor 104 may include the same components as discussed above in conjunction with the FIG. 9 embodiment and further may include additional components. The controller 218 may receive input from an on/off switch 226, a clock set switch or switches 228, a compliance programming input 230, and the compliance sensor 106. Input from the compliance sensor 106 may be received by the controller 218 through an analog-to-digital converter (ADC) 234. The controller 218 may provide outputs to a compliance display 236 as discussed below.

The controller 218 may receive and store a compliance protocol for the medical device 102 for determining wear compliance through a compliance programming input 230. The compliance programming input 230 may be similar to a clock set switch where a sequence of buttons are depressed to program the compliance protocol in the compliance monitor 104 or the compliance programming input may include a connection, such as those used with the interface 238, with a computer 216 for uploading the compliance protocol. Some of the criteria used in the protocol may include the amount of time the medical device is to be worn over a period of time such as a day, week, month, etc. as well as during activities or at rest.

The controller 218 may receive data from the compliance sensor 106 as a function of time and compare the data with the compliance protocol to produce compliance data to determine if the collected data meets the requirements of the compliance protocol and thus, if the patient is in compliance with the protocol. The comparison is preferably made in a continuous fashion and may be readily available so that the patient may know as soon as possible if they are in compliance with the protocol.

Figure 11:
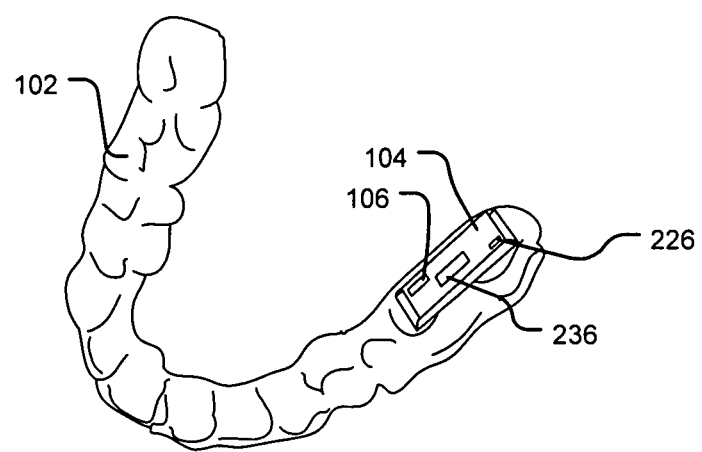
FIG. 11 shows a further embodiment of an orthodontic device and compliance monitor of the invention having a display for displaying compliance data.

The controller 218 may provide compliance output information such as data from the compliance sensor 106 and compliance data to a separate compliance display 236. With reference to FIG. 10, the compliance display 236 may be an LCD or other known display screen that displays information to the patient such as the amount of time the medical device has been worn, how much longer the medical device must be worn, and whether the compliance conditions are being met. The display 236 may also provide information such as the average daily wear time as well as current wear time for the medical device. The compliance display may alternatively or additionally include an LED light or series of LED lights that indicate to the patient whether the compliance conditions of the protocol are being met. For example, a green LED may illuminate when the compliance conditions are being met and a red LED 46 may illuminate for noncompliance conditions. Moreover, these LEDs may illuminate in response to pressing a discreet button to conserve power such as the on/off switch 226. FIG. 11 shows an embodiment of the orthodontic device 102 and compliance monitor 104 of the invention having a display 236 for displaying compliance data.

The compliance display 236 may be located in a position that can be easily monitored. In preferred embodiments, the compliance display 236 is located at a visible location on the medical device 102. In alternative embodiments, the compliance display 236 may be located remotely from the medical device 102 by wire or wireless connections with the compliance monitor 104.

In some instances it will be useful to monitor other properties associated with the wearing of a medical device 102. For example, to be able to distinguish what the patient was doing while wearing the medical device 102 may help with treatment and provide health care providers additional important information regarding the treatment of the patient. Accordingly, with reference to FIG. 10, in certain embodiments of the invention, it may be advantageous to provide at least one secondary sensor 242 that may monitor properties other than whether the medical device is being worn or not. The secondary sensor 242 may include, but is not limited to, a tilt sensor, an acceleration sensor, a velocity sensor, a pressure, or force sensor. The secondary sensor 242 may be located on an appropriate position on the medical device 102 for the type of sensor being used. The secondary sensor 242 may be secured to the medical device and attached to the compliance monitor 104 through the ADC 234 for secondary data collection and storage. By collecting information from the secondary sensor in conjunction with the compliance sensor 106, the additional compliance dimension may be monitored by the health care provider and the patient.

Figure 12:
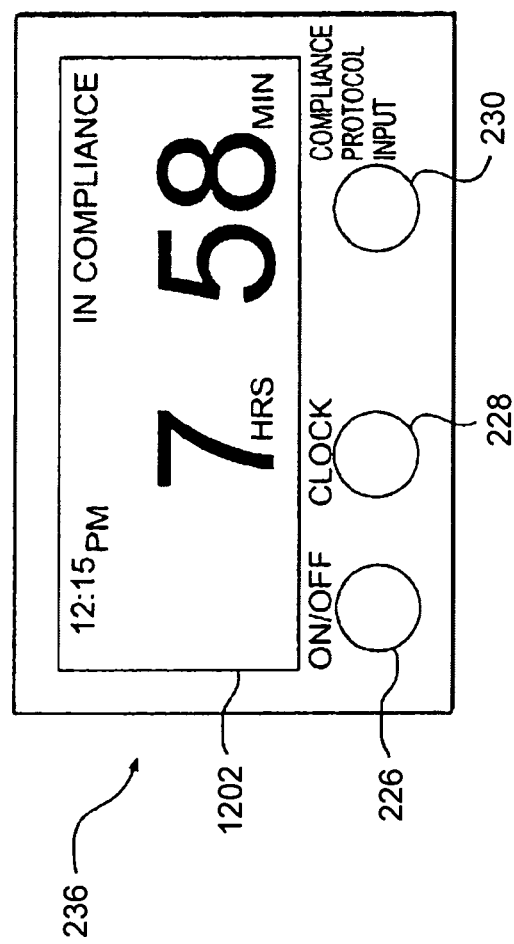
FIG. 12 shows a display constructed in accordance with one embodiment of the invention that may be used with the compliance monitor.

With reference now to FIG. 12, the compliance display 236 may be an LCD screen 1202 or the like that displays information to the patient such as the amount of time the brace has been worn, how much longer the brace must be worn, and whether the compliance conditions are being met. The display 236 may also provide information such as the average daily wear time as well as current wear time for the brace.

Figure 13:
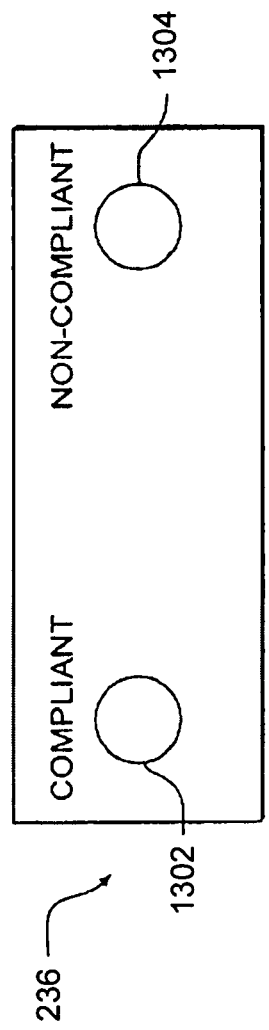
FIG. 13 shows another embodiment of a display panel for the compliance monitor constructed in accordance with the principles of the invention that may be used with the compliance monitor.

With reference to FIG. 13, the compliance display 236 may include an LED or series of LEDs that indicate to the patient weather the compliance conditions of the protocol are being met. For example, a green LED 1302 would illuminate if the compliance conditions are being met and a red LED 1304 would illuminate for noncompliance conditions.

Alternatively, the compliance monitor may also be implemented as a reactive chemical that is arranged on the medical device 102 and may be in physical contact with, for example, saliva in the mouth. The amount of time the medical device 102 is used, the more the chemical reacts or is worn off the medical device 102. Accordingly, the chemical may be coated on a surface and the amount of chemical remaining on the surface after a given time will be indicative of the amount of time the device was used.

In accordance with various embodiments of the invention, the methods described herein are intended for operation with dedicated hardware implementations including, but not limited to, semiconductors, application specific integrated circuits, programmable logic arrays, and other hardware devices constructed to implement the methods and modules described herein. Moreover, various embodiments of the invention described herein are intended for operation with as software programs running on a computer processor. Furthermore, alternative software implementations including, but not limited to, distributed processing or component/object distributed processing, parallel processing, virtual machine processing, any future enhancements, or any future protocol can also be used to implement the methods described herein.

It should also be noted that the software implementations of the invention as described herein are optionally stored on a tangible storage medium, such as: a magnetic medium such as a disk or tape; a magneto-optical or optical medium such as a disk; or a solid state medium such as a memory card or other package that houses one or more read-only (non-volatile) memories, random access memories, or other re-writable (volatile) memories. A digital file attachment to email or other self-contained information archive or set of archives is considered a distribution medium equivalent to a tangible storage medium. Accordingly, the invention is considered to include a tangible storage medium or distribution medium, as listed herein and including art-recognized equivalents and successor media, in which the software implementations herein are stored While the invention has been described in terms of exemplary embodiments, those skilled in the art will recognize that the invention can be practiced with modifications in the spirit and scope of the appended claims. These examples given above are merely illustrative and are not meant to be an exhaustive list of all possible designs, embodiments, applications, or modifications of the invention.

What is claimed:

1. An orthodontic compliance monitor, comprising:
    a sensor that senses when an orthodontic appliance is positioned in the mouth for use;
    a processor that processes an output of said sensor and generates compliance data based on a compliance protocol; and
    a memory device that stores the compliance data.

2. The orthodontic compliance monitor of claim 1, wherein said sensor comprises at least one of a temperature sensor, pressure sensor, moisture sensor, light sensor, or pH sensor.

3. The orthodontic compliance monitor of claim 1, wherein said processor comprises at least one of a micro controller, microprocessor, application specific integrated circuit, counter, or field programmable gate array.

4. The orthodontic compliance monitor of claim 1, further comprising an interface configured to output the compliance data as at least one of radio frequency signals, optical signals, or electrical signals.

5. The orthodontic compliance monitor of claim 1, further comprising an output device configured to output compliance data.

6. The orthodontic compliance monitor of claim 5, wherein said output device comprises a display that displays the compliance data.

7. The orthodontic compliance monitor of claim 1, wherein said compliance protocol comprises an amount of time the orthodontic appliance is to be worn over a period of time.

8. The combination of an orthodontic appliance and the orthodontic compliance monitor of claim 1.

9. The combination of claim 8, wherein said orthodontic appliance is one of an orthodontic brace, a retainer, a mouth guard, a bruxism treatment device, and a nightguard.

10. The orthodontic compliance monitor of claim 1, wherein the compliance monitor is configured to be at least one of removably coupled with an orthodontic appliance or physically incorporated into an orthodontic appliance.

11. A method of determining whether a user is using an orthodontic appliance, said method comprising the steps of:
    sensing, using an electronic sensor positioned in the user's mouth, when an orthodontic appliance is positioned for use in a user's mouth to generate a digital output;
    processing the output and generating compliance data based on a compliance protocol; and
    storing the compliance data.

12. The orthodontic compliance monitor method of claim 11, wherein said step of sensing comprises sensing at least one of temperature, pressure, moisture, light, or pH.

13. The orthodontic compliance monitor method of claim 11, further comprising the step of:
    transmitting the compliance data as at least one of radio frequency signals, optical signals, or electrical signals.

14. The orthodontic compliance monitor method of claim 11, further comprising the step of:
displaying the compliance data.

15. A computerized orthodontic compliance system, comprising:
a sensor that senses when an orthodontic appliance is positioned in the mouth for use;
a processor that processes an output of said sensor and generates compliance data based on a compliance protocol;
a memory that stores the compliance data; and
a computer configured to receive the compliance data from said memory.

16. The system of claim 15, further comprising an interface configured to output the compliance data as at least one of radio frequency signals, optical signals, or electrical signals to said computer.

17. The system of claim 15, wherein said sensor comprises at least one of a temperature sensor, pressure sensor, moisture sensor, light sensor, or pH sensor.

18. The system of claim 15, wherein said processor comprises at least one of a micro controller, microprocessor, application specific integrated circuit, counter, or field programmable gate array.

19. The system of claim 15, further comprising an interface configured to transmit the compliance data as at least one of radio frequency signals, optical signals, or electrical signals.

20. The system of claim 15, further comprising an output device configured to output the compliance data.

21. A non-transitory computer readable medium having computer executable code that executes orthodontic compliance monitor processing comprising:
sensing when an orthodontic appliance is positioned in the mouth for use to generate an output;
processing the output and generating compliance data based on a compliance protocol; and
storing compliance data.

22. The non-transitory computer readable medium according to claim 21 wherein the executable code executes orthodontic compliance monitor processing further comprising:
transmitting the compliance data as at least one of radio frequency signals, optical signals, or electrical signals.

23. The non-transitory computer readable medium according to claim 21 wherein the executable code executes orthodontic compliance monitor processing further comprising displaying the compliance data.

24. An orthodontic compliance monitor, comprising:
means for sensing when an orthodontic appliance is positioned in the mouth for use;
means for processing an output of said sensor means and for generating compliance data based on a compliance protocol; and
means for storing the compliance data.

25. An orthodontic appliance compliance monitor, comprising:
an orthodontic appliance comprising one of an orthodontic brace, a retainer, a mouth guard, a bruxism treatment device, and a nightguard;
means for determining when an orthodontic appliance is positioned in the mouth for use arranged on said orthodontic appliance, wherein said determining means generates an output; and
means for comparing the output with a stored compliance protocol to generate compliance data that indicate whether the data from the compliance sensor meets the requirements of the compliance protocol,
wherein said determining means comprises one of a sensor or reactive chemical.

26. The computerized orthodontic compliance system of claim 15, wherein the processor is included in a compliance monitor attached to the orthodontic appliance.

27. A method of determining whether a user is using an orthodontic appliance, said method comprising the steps of:
sensing using a compliance sensor, when an orthodontic appliance is positioned for use in a user's mouth to generate an output;
receiving, by a controller in communication with the orthodontic appliance, data from the compliance sensor;
sending the data received from the compliance sensor to a computer;
displaying the data from the compliance sensor; and
processing the data from the compliance sensor and generating compliance data based on a compliance protocol.

28. The method of claim 27, wherein the step of displaying the data from the compliance sensor comprises displaying the data from the compliance sensor on the computer.

29. The method of claim 27, wherein the step of displaying the data from the compliance sensor comprises displaying the data from the compliance sensor on the appliance.

30. The method of claim 27, further comprising displaying the compliance data.

31. The method of claim 30, wherein the step of displaying the compliance data comprises displaying the compliance data on the appliance.

32. The method of claim 30, wherein the step of displaying the compliance data comprises displaying the compliance data on the computer.

33. The method of claim 27, further comprising storing the compliance data.

34. The method of claim 27, wherein the step of processing the data from the compliance sensor and generating compliance data based on a compliance protocol comprises processing the data from the compliance sensor and generating compliance data by the controller.

35. The method of claim 27, wherein the compliance data indicates whether the data from the compliance sensor meets the requirements of the compliance protocol.

36. The method of claim 27, wherein the compliance protocol specifies an amount of time the orthodontic appliance is to be worn over a period of time.

37. A computerized orthodontic compliance system, comprising:
a computer;
a sensor that senses when an orthodontic appliance is positioned in the mouth of a user for use;
a controller in communication with the orthodontic appliance, wherein the controller receives data output from the compliance sensor and provides the data to the computer through an interface;
a processor that processes data output from said sensor and generates compliance data based on a compliance protocol; and
a memory that stores the compliance data.

38. The computerized orthodontic compliance system of claim 37, wherein said processor is located in said controller.

39. The computerized orthodontic compliance system of claim 37, wherein said computer includes an output device that displays information indicative of whether compliance conditions are being met.

40. The computerized orthodontic compliance system of claim 37, wherein the orthodontic device includes an output device that displays information indicative of whether compliance conditions are being met.

41. The computerized orthodontic compliance system of claim 37, wherein the interface is wireless.

42. The computerized orthodontic compliance system of claim 37, wherein the compliance data indicates whether the data from the compliance sensor meets the requirements of the compliance protocol.

43. The computerized orthodontic compliance system of claim 37, wherein the compliance protocol specifies the amount of time the orthodontic appliance is to be worn over a period of time.

* * * * *